US006983923B2

(12) United States Patent
Fukui et al.

(10) Patent No.: US 6,983,923 B2
(45) Date of Patent: Jan. 10, 2006

(54) FLOW CONTROL VALVE

(75) Inventors: Ryoichi Fukui, Kyoto (JP); Hisatomi Matsuda, Kyoto (JP)

(73) Assignee: Omron Corporation, Kyoto (JP)

( * ) Notice: Subject to any disclaimer, the term of this patent is extended or adjusted under 35 U.S.C. 154(b) by 142 days.

(21) Appl. No.: 10/312,146

(22) PCT Filed: Jun. 20, 2001

(86) PCT No.: PCT/JP01/05290

§ 371 (c)(1),
(2), (4) Date: Dec. 23, 2002

(87) PCT Pub. No.: WO01/98696

PCT Pub. Date: Dec. 27, 2001

(65) Prior Publication Data
US 2003/0120157 A1 Jun. 26, 2003

(30) Foreign Application Priority Data
Jun. 22, 2000 (JP) ............................. 2000-187079

(51) Int. Cl.
*F16K 31/08* (2006.01)

(52) U.S. Cl. .................. 251/65; 335/229; 335/256
(58) Field of Classification Search ............... 251/65, 251/129.15, 129.1, 129.09; 335/229, 256
See application file for complete search history.

(56) References Cited

U.S. PATENT DOCUMENTS

| 2,637,343 | A | * | 5/1953 | Matthews ................... 251/65 |
| 3,504,320 | A | | 3/1970 | Engdahl et al. | |
| 4,128,105 | A | * | 12/1978 | Follett ....................... 251/65 |
| 4,245,815 | A | * | 1/1981 | Willis ................... 251/129.08 |
| 4,459,991 | A | | 7/1984 | Hatschek | |
| 5,434,549 | A | | 7/1995 | Hirabayashi et al. | |
| 5,820,104 | A | * | 10/1998 | Koyano et al. ............... 251/65 |
| 5,947,155 | A | | 9/1999 | Miki et al. | |
| 6,386,505 | B2 | * | 5/2002 | Schob ......................... 251/65 |

FOREIGN PATENT DOCUMENTS

| DE | 1 808 900 | 6/1969 |
| DE | 19636781 A1 | 3/1998 |
| GB | 1 252 913 | 11/1971 |
| GB | 2107189 A | 4/1983 |
| JP | 63-50012 | 7/1984 |
| JP | 63-50012 | 10/1988 |
| JP | 6-47008 | 2/1994 |
| JP | 6-315255 | 11/1994 |
| JP | 7-274468 | 10/1995 |
| JP | 08-285116 | 11/1996 |

(Continued)

*Primary Examiner*—John Bastianelli
(74) *Attorney, Agent, or Firm*—Morrison & Foerster LLP

(57) ABSTRACT

A flow control valve utilizing at least one permanent magnet and at least one magnetic coil, wherein one or more permanent magnets or magnetic coils are used to move a movable member in towards and/or away from an inflow port so as to control the flow through the port. When multiple permanent magnets are used, at least one yoke, which protrudes beyond the edges of the magnets, is place between each pair of magnets. A fixed shaft that passes through a hollow portion of the movable member is used to control the movement of the movable member, and an air vent is present near the end of the movable member that is closest to the inflow port such that the hollow space of the movable member does not form a vacuum.

3 Claims, 12 Drawing Sheets

FOREIGN PATENT DOCUMENTS

| | | |
|---|---|---|
| JP | 9-172478 | 6/1997 |
| JP | 10-196832 | 7/1998 |
| JP | 2596857 | 4/1999 |
| JP | 2595510 | 5/1999 |
| JP | 2596857 | 6/1999 |
| JP | 10-196832 | 9/1999 |
| JP | 11-248025 | 9/1999 |
| JP | 2000-346230 | 12/2000 |

* cited by examiner

FLOW CONTROL VALVE

TECHNICAL FIELD

The present invention relates to a flow control valve for use as air exhaust means of a blood pressure gauge, for example, and a blood pressure gauge provided with the relevant flow control valve.

BACKGROUND ART

Among a variety of blood pressure gauges having been proposed, one is configured to increase the pressure within the cuff to a predetermined level and then gradually decrease the pressure, during which the blood pressure of the subject is measured. A flow control valve for use in such a blood pressure gauge to gradually decrease the pressure within the cuff is disclosed, e.g., in Japanese Patent Laying-Open No. 6-47008 titled "Flow Control Valve". The flow control valve described therein includes a front case with a pressure inflow port (gas inflow port) and a pressure outflow port (gas outflow port) formed therein. A driving shaft is supported such that it can move toward and away from the gas inflow port, and an orifice packing is attached to a portion of the driving shaft opposite to the gas inflow port. A magnet coil is further attached to the driving shaft, and a plate and a yoke excited by a permanent magnet are arranged around the magnet coil. The front and back portions of the driving shaft are connected to a frame portion via front and back dampers, respectively.

With this flow control valve, when current is passed through the magnet coil, the driving shaft moves together with the magnet coil by an electromagnetic force generated by the permanent magnet and the magnet coil, and the orifice packing closes the gas inflow port. This kind of control valve is called a "moving coil type", since the magnet coil moves.

The flow control valve of this type, however, is disadvantage in that it has many complex parts and requires manpower for assembly, hindering the use of an auto-assembly machine. This increases the parts cost and degrades the productivity.

To solve such problems, the applicant conceived a flow control valve as shown in FIG. 15A (schematic cross sectional view) and FIG. 15B (left side view), and filed an earlier application (Japanese Patent Application No. 2000-31920). The flow control valve disclosed therein is of a moving magnet type with a permanent magnet made to move.

In the flow control valve shown in FIGS. 15A and 15B, a housing is formed of a front cap 2, a front case 8 and a frame lid 10. The housing has a gas inflow port 1a with an inner tube 1 of a nozzle form opening within, and a gas outflow port 1b communicating with gas inflow port 1a via an internal space. An actuating shaft 4 is arranged within the housing such that it can move toward and away from inflow port 1a. An orifice packing 3 is attached to an end 4a of actuating shaft 4 opposite to inflow port 1a so that the movement of actuating shaft 4 opens and closes inflow port 1a. A permanent magnet 5 is provided to press actuating shaft 4. Permanent magnet 5 is movably passed through a hollow portion of a bobbin 7 provided with a magnet coil 6. Magnet coil 6 is connected to an external terminal 11. Actuating shaft 4 is configured to move leftward in FIG. 15A by an electromagnetic force generated by permanent magnet 5 and magnet coil 6.

Further, actuating shaft 4 is connected to front cap 2 via a damper 9. Damper 9 biases the shaft 4 to the right direction of FIG. 15A. The end surface of orifice packing 3 and the opening surface of inflow port 1a are both flat. The end surface of orifice packing 3 is made diagonal (non-parallel) to the opening surface of inflow port 1a, at an angle of, e.g., 3°. The hollow portion of bobbin 7 has a wall serving as a stopper of permanent magnet 5, and an air vent 7b is formed to allow smooth movement of permanent magnet 5.

A case where the flow control valve configured as described above is utilized for measurement of blood pressure is now described by way of example. The schematic configuration of the blood pressure gauge is shown in FIG. 13, and the relevant flow control valve is used as a gradual exhaust valve 36 in FIG. 13. Firstly, a current of a predetermined level is passed through magnet coil 6 to generate an electromagnetic force by the interaction with permanent magnet 5. This electromagnetic force causes permanent magnet 5 to move to the left, thereby pressing actuating shaft 4. Correspondingly, orifice packing 3 at the end 4a of the actuating shaft is pressed to contact inflow port 1a, so that inner tube 1 attains a completely blocked state.

Next, under the blocked state, a pump is activated to introduce air into a cuff for pressurization. This is followed by a cuff depressurizing process, during which a current supplied to magnet coil 6 is gradually decreased to progressively reduce a thrust by the electromagnetic force. Accordingly, orifice packing 3 moves to the right direction by means of the spring action of damper 9 and the slant repulsive action of orifice packing 3. This gradually opens inflow port 1a, and the air within the cuff is exhausted very slowly into the atmosphere from inflow port 1a via outflow port 1b. The blood pressure of the subject is measured during this process.

As described above, with the flow control valve shown in FIGS. 15A and 15B, the thrust by the electromagnetic force generated at magnet coil 6 is used to shut inflow port 1a, and the repulsive forces of damper 9 and of orifice packing 3 itself are used to open inflow port 1a. The thrust by the electromagnetic force and the repulsion forces are transmitted to orifice packing 3 via permanent magnet 5 and actuating shaft 4. The structure shown in FIGS. 15A and 15B, however, is disadvantageous in that it cannot effectively utilize the thrust by the electromagnetic force generated by magnet coil 6. The flow control valve requiring large valve load (pressing force of orifice packing 3 against inflow port 1a) would increase in size and require huge electric power.

In other words, with the flow control valve shown in FIGS. 15A and 15B, the force to press orifice packing 3 against inflow port 1a is not so strong. Such a weak pressing force is insufficient for a blood pressure gauge applied to the arm which receives greater pressure than a blood pressure gauge applied to the wrist, possibly resulting in insufficient blocking of inflow port 1a when pressurizing the cuff to a level greater than maximum blood pressure. If it is attempted to increase the pressing force to avoid this unfavorable situation, the flow control valve would become large, and the consumed power would increase accordingly.

Further, with the flow control valve shown in FIGS. 15A and 15B, brittle permanent magnet 5 would often get chipped due to shock of drop or the like, resulting in poor controllability of the flow rate.

DISCLOSURE OF THE INVENTION

The present invention has been made focusing on the conventional problems as described above. Its object is to provide a flow control valve which fully derives and effectively utilizes a thrust by an electromagnetic force despite a simple structure, and which is compact and consumes less power and suffers less malfunction.

To achieve the above object, the inventors investigated the documents of the past and aimed at an electromagnetic apparatus described in German Patent No. 1808900 (filed Nov. 14, 1968) among them. The electromagnetic apparatus described in the relevant German Patent has the following structure. A coil formed of three winding wires has a hollow at the center of which a core formed of two permanent magnets is arranged coaxially as well as movably in the axial direction. The winding direction of the winding wires at the both ends is opposite to the winding direction of the winding wire at the center, and the permanent magnets are arranged with their magnetic poles directed in the opposite directions (such that the same poles confront each other).

Taking notice of the large thrust of the core obtained by this electromagnetic apparatus, and in an attempt to adapt it to the flow control valve for use in a blood pressure gauge or the like, the inventors of the present invention carried on the investigation with a continuous process of try and error and finally completed the present invention.

Specifically, the flow control valve of the present invention includes: a housing having a gas inflow port and a gas outflow port communicating with the gas inflow port through an internal space; a moving member arranged inside the housing such that it can move toward and away from said gas inflow port; an open/close member arranged on a portion of the moving member opposite to the gas inflow port such that the movement of the moving member opens/closes said gas inflow port; and a magnetic coil and a permanent magnet arranged within the housing to move the moving member. The moving member is made to move with an electromagnetic force generated by said magnet coil and said permanent magnet such that the gas inflow port is opened/closed by the open/close member to control an air flow rate. The flow control valve is characterized in that at least one of either one of said magnet coil and said permanent magnet and a plurality of the other are used, and, in the case where a plurality of permanent magnets are used, the permanent magnets are arranged such that the same poles confront each other, and in the case where a plurality of magnet coils are used, winding directions of the respective magnet coils are set to change the directions in which current flows through the respective magnetic coils such that the moving member receives a combined force of the electromagnetic forces generated by the respective magnet coils and the at least one permanent magnet in a direction along which the moving member moves, so that the electromagnetic forces generated by the respective magnet coils and the at least one permanent magnet are combined to be used as a thrust of the moving member.

This flow control valve uses at least one of either one of the magnet coil and the permanent magnet, and a plurality of the other of the magnet coil and the permanent magnet. Possible combinations are, as will be described in conjunction with embodiments of the present invention later, a combination of two permanent magnets and three magnet coils (see FIGS. 1A and 1B), a combination of one permanent magnet and two magnet coils (see FIGS. 9A and 9B), a combination of four permanent magnets and five magnet coils (see FIGS. 10A and 10B), and a combination of two permanent magnets and one magnet coil (see FIGS. 11A and 11B). However, any other combinations are possible.

When a plurality of permanent magnets are being used, they are arranged such that the repelling, same poles (N poles or S poles) confront each other. When a plurality of magnet coils are being used, the winding directions of the respective magnet coils are set such that the moving member receives a combined force of the electromagnetic forces generated by the respective magnet coils and the at least one permanent magnet in a direction along which it moves. More specifically, in the case where a plurality of magnet coils are being axially arranged in series, when the winding direction of an arbitrary magnet coil is in a right direction, the winding direction of the neighboring magnet coil is set to a left direction. That is, the winding directions are made alternately opposite to each other such that the current flows in the opposite directions through the neighboring magnet coils.

Since the electromagnetic forces generated by respective permanent magnets and respective magnet coils can be combined to actuate the moving member, the thrust to move the moving member increases considerably compared to the conventional case where only one permanent magnet and one magnet coil are used, and the open/close member attached to the moving member can press the gas inflow port with a remarkably strong force. As a result, the thrust of the moving member can be increased with the structure of the conventional size, or the structure can be downsized when the thrust of the conventional level will suffice. Accordingly, a flow control valve which can fully derive and effectively utilize a thrust by an electromagnetic force in spite of a simple structure, and which is compact and consumes less power and suffers less malfunction, is provided.

In the flow control valve of the present invention, if a plurality of permanent magnets are being used, the same poles of the magnets are made to face each other. When the same poles are arranged next to each other, the permanent magnets repel each other, making the assembly extremely difficult. However, when a yoke made of a magnetic substance is arranged between the permanent magnets, the respective magnets attract the yoke, so that the repelling force is almost nullified. This leads to simplification of the assembly and effective utilization of the magnetic forces of the permanent magnets. Even if one permanent magnet is being used, the yoke is preferably arranged on one side (e.g., N pole side) of the magnet, since the yoke has a function to efficiently collect magnetic flux of the magnet coil. Use of the yoke allows effective utilization of the magnetic force.

In the case where a yoke is being arranged between permanent magnets, it is preferable that the yoke has end surfaces that protrude outward from the opposing surfaces of the permanent magnets. If the end surfaces of the yoke have the same size as the opposing surfaces of the permanent magnets, it would be more or less affected by the repelling action of the same poles of the permanent magnets. The end surfaces of the yoke projecting outward from the opposing surfaces of the permanent magnets further facilitate the arrangement of the permanent magnets with the same poles facing each other.

The permanent magnets and the yoke may be arranged in series and attached to the moving member such that they move together with the moving member. In this case, the permanent magnets and the yoke move together with the moving member as the moving member moves by the thrust by the electromagnetic force.

Although the shapes of the magnet coil and the permanent magnet are unspecified, one possible way is to form the moving member in a cylindrical shape and the magnet coil and the permanent magnet each in a ring shape. If the ring-shaped permanent magnet is attached to the outer circumferential surface of the cylindrical moving member, and the ring-shaped magnet coil is arranged outside the permanent magnet, then the moving member, the magnet coil and the permanent magnet will be placed concentrically. This facilitates the assembly of the three parts of moving member, magnetic coil and permanent magnet, and also allows more efficient utilization of the electromagnetic force, and the thrust of the moving member can be derived to the fullest extent.

The moving member moves by the electromagnetic force generated by the magnet coil and the permanent magnet. It moves frontward until the open/close member abuts the inflow port, and moves backward until the moving member contacts, e.g., a stopper provided to the housing. If the permanent magnet is integrally attached to the moving member, the permanent magnet will experience a strong impact when the moving member comes to a halt or the housing is dropped, and may get chipped or break because of its brittleness. Thus, elastic bodies are preferably arranged opposite to outer end surfaces of the permanent magnets located at both outer ends of the permanent magnets arranged in series. The elastic bodies will absorb the impact, thereby avoiding chipping or the like of the permanent magnets.

Although the elastic bodies having flat end surfaces can be used, the elastic bodies themselves and the parts placed between the elastic bodies practically vary in dimension, which may cause gaps (making the parts unstable) even if the elastic bodies are employed, hindering effective shock absorption. To avoid such a problem, readily deformable projection(s) may be provided on one or both end surfaces of each elastic body. The extent of protrusion of the projections is preferably set greater than total dimensional variation of the elastic bodies themselves and the parts placed between the elastic bodies. In this case, the projections will be deformed to prevent the parts from jouncing as long as the parts dimension is within the range of variation. The projections may be arranged continuously or distributed over the end surface(s) as long as the pressure generated upon deformation is distributed in balance. In either case, all that is needed is to absorb the dimensional variation of the elastic bodies and the parts placed therebetween by the deformation of the projections.

The moving member moving by the electromagnetic force preferably exhibits good response to current application to the magnet coil. That is, the moving member is made to rapidly move upon application of the current to the magnet coil to cause the open/close member to block the gas inflow port immediately. To this end, a fixed shaft may be provided which guides the moving member to move only in directions to open and close the gas inflow port. With this configuration, the moving member linearly moves along the fixed shaft towards and away from the gas inflow port, with wasteful movement and jouncing being eliminated. When applied to a blood pressure gauge, minute and continuous control of the exhaust flow rate becomes possible, with excellent operative reproducibility.

As the fixed shaft, any shaft completely unaffected or hardly affected by the permanent magnet(s) may be utilized, which may be made of, e.g., nonmagnetic metal, resin or glass. Since the fixed shaft is only required to movably support the moving member, it may have a cross section of any shape such as a perfect circle, ellipse, polygon or the like. Further, the number of the fixed shafts is not limited to one. Two or more fixed shafts may be used to support the moving member.

However, by making the moving member hollow and passing the fixed shaft through the hollow portion of the moving member, the moving member and the fixed shaft can be arranged efficiently without wasting a space. In this case, the fixed shaft can guide the moving member over a substantial portion thereof, and the structure is also simplified. The moving member and the fixed shaft may be secured to each other in any manner, e.g., by insert molding of the parts other than the moving member into a resin portion, by fixing with a retaining ring (e.g., E-ring, clip retaining ring), or with a screw.

Further, by forming the fixed shaft integrally with the magnet coil, in the case where the moving member, magnet coil and permanent magnet are arranged to form rings in cross section as described above, the four parts including the fixed shaft can be arranged efficiently. Of course, this configuration allows effective utilization of the electromagnetic force.

On the other hand, when the fixed shaft is being passed through the hollow portion of the moving member, the moving member is preferably provided with an air vent which communicates the hollow portion of the moving member with the internal space of the housing, because of the following reasons. When the moving member moves to a direction exposing the fixed shaft (i.e., when it moves toward the gas inflow port), the hollow portion of the moving member is almost blocked by the fixed shaft. Negative pressure is thus produced in the hollow portion, which acts as counterforce against the movement of the moving member. On the contrary, when the moving member moves to a direction receiving the fixed shaft (i.e., when it moves away from the gas inflow port), the air within the hollow portion of the moving member is compressed by the fixed shaft, so that counterforce against the movement of the moving member is again produced.

Thus, the air vent is provided to the moving member, which ensures smooth movement of the moving member in the absence of air resistance, since the air within the hollow portion is unaffected by expansion, compression or other phenomena.

As described above, the flow control valve of the present invention fully derives and effectively utilizes the thrust by the electromagnetic force in spite of its simple structure, and is compact and consumes less power and suffers less malfunction. This flow control valve is optimally applied as air exhaust means of a blood pressure gauge, for example.

BEST MODES FOR CARRYING OUT THE INVENTION

Hereinafter, the present invention will be described with reference to the embodiments.

Figure 1A:
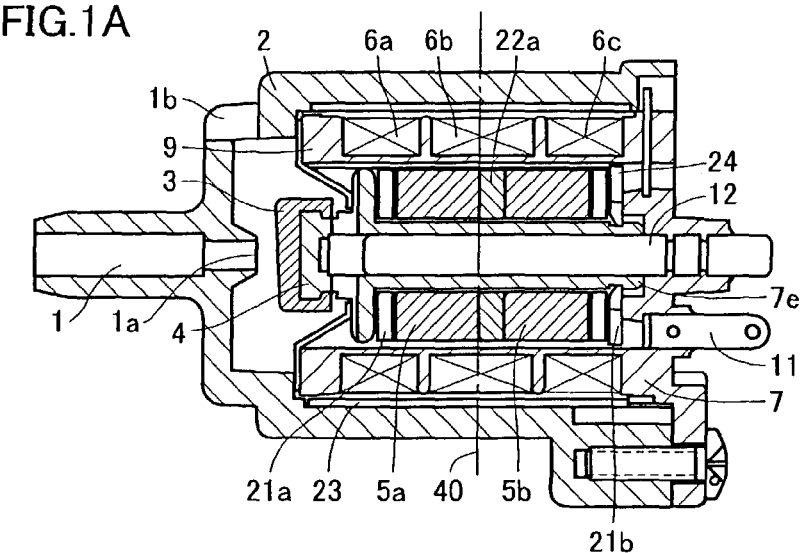
FIGS. 1A and 1B are a schematic cross sectional view and a left side view, respectively, of a flow control valve according to an embodiment of the present invention.
Figure 1B:
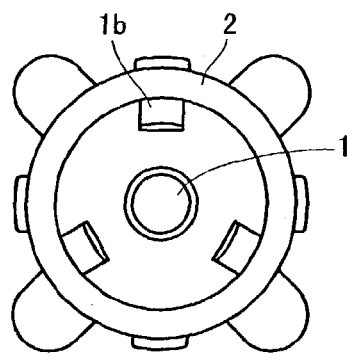
Figure 15A:
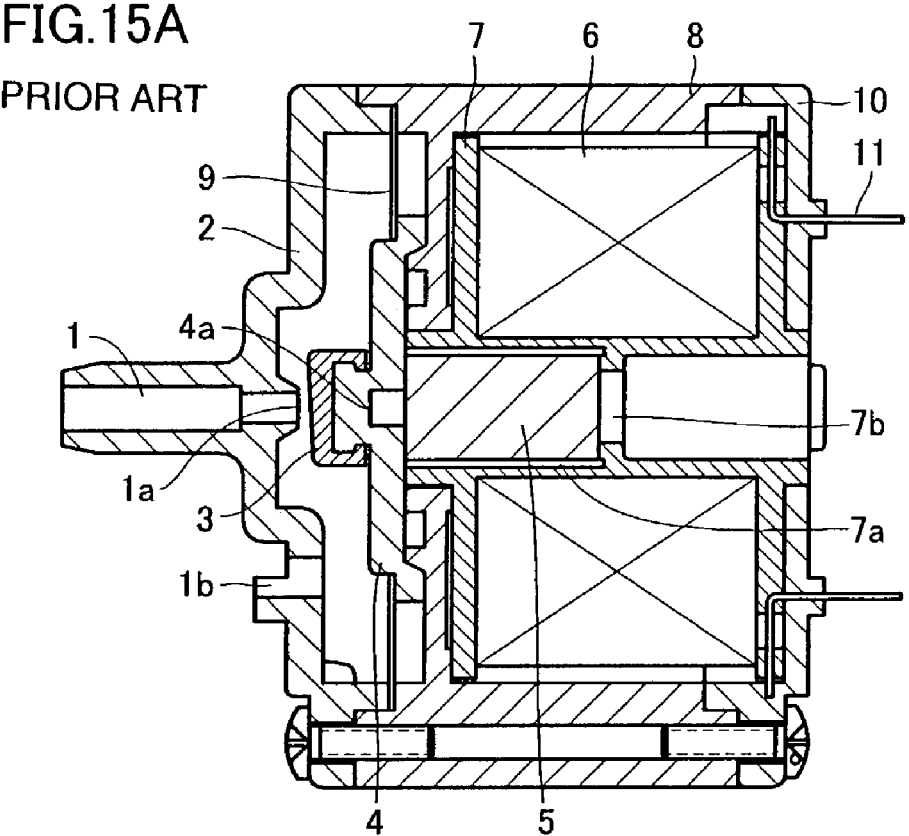
FIGS. 15A and 15B are a schematic cross sectional view and a left side view, respectively, of the flow control valve according to a conventional example.
Figure 15B:
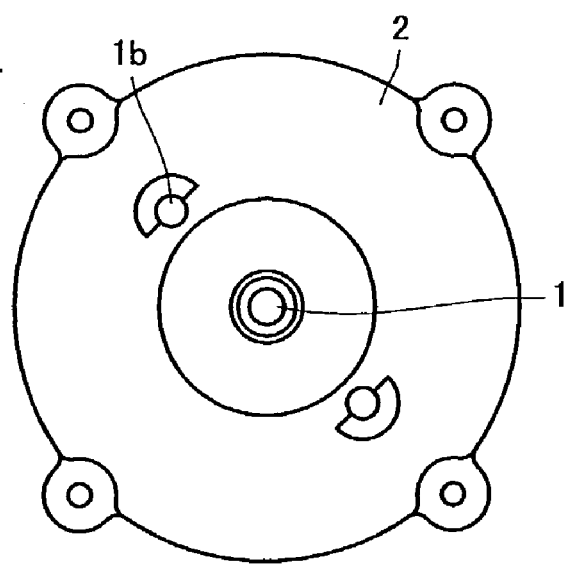

The flow control valve according to one of the embodiments is shown in FIG. 1A (schematic cross sectional view) and FIG. 1B (left side view), wherein the same elements as those in FIGS. 15A and 15B are denoted by the same reference characters.

The flow control valve of the present embodiment uses two permanent magnets 5a, 5b and three magnet coils 6a, 6b, 6c. A frame case 2 corresponding to the aforementioned front cap and a rear portion of the bobbin 7 constitute a housing. This housing (frame case 2) is provided with a gas inflow port 1a having an inner tube 1 of a nozzle form opening within, and a plurality of (in this example, three) gas outflow ports 1b communicating with gas inflow port 1a via an internal space.

Figure 2A:
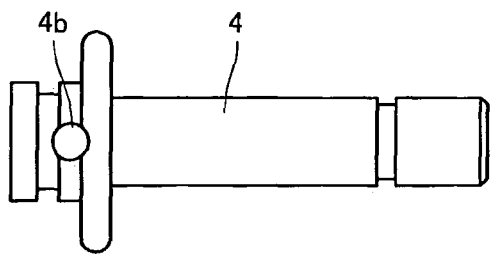
FIGS. 2A and 2B are a top plan view and a partially cutaway view, respectively, of an actuating shaft of the relevant flow control valve.
Figure 2B:
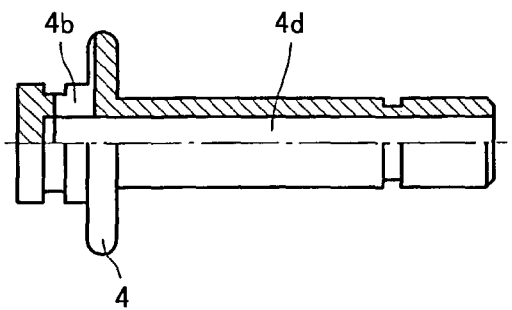
Figure 8A:
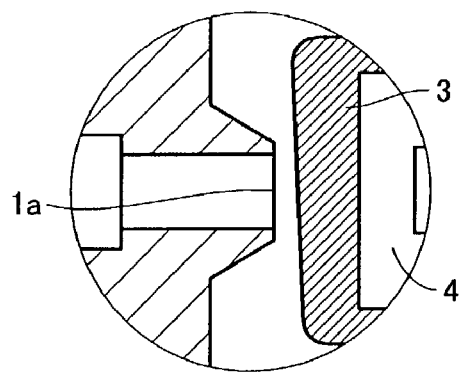
FIG. 8A is a partial enlarged cross sectional view showing an orifice packing completely opening an gas inflow port.
Figure 8B:
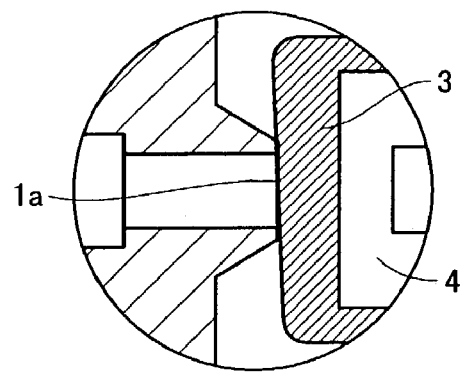
FIG. 8B is a partial enlarged cross sectional view showing the orifice packing completely blocking the gas inflow port, in the relevant flow control valve.

In this housing, a hollow actuating shaft (moving member) 4 as shown in FIGS. 2A, 2B is arranged such that it can move toward and away from inflow port 1a. An orifice packing (open/close member) 3 is attached to an end of the actuating shaft opposite to inflow port 1a so that the movement of actuating shaft 4 opens/closes inflow port 1a. As shown in the partial enlarged cross sectional views of FIGS. 8A, 8B (FIG. 8A showing the open state and FIG. 8B showing the closed state), the end surface of orifice packing 3 and the opening of inflow port 1a are both flat, and the end surface of orifice packing 3 is set diagonal (non-parallel) to the opening of inflow port 1a, at an angle of, e.g., 3°.

Referring to FIGS. 2A, 2B, actuating shaft 4 has an air vent 4b which communicates its hollow portion 4d with the internal space of the housing. A non-magnetic fixed shaft 12 is passed through the hollow portion 4d of actuating shaft 4. Fixed shaft 12 is fixed integrally to bobbin 7. Permanent magnets 5a, 5b, a yoke 22a and elastic bodies 21a, 21b are secured on the outer circumference of actuating shaft 4 by means of a retaining ring 24, so that actuating shaft 4 moves together with permanent magnets 5a, 5b, yoke 22a and others. Actuating shaft 4 linearly moves along the fixed shaft 12. It is movable in one direction until orifice packing 3 contacts and completely shuts inflow port 1a, and in the other direction until the rear end portion of actuating shaft 4 abuts a stopper 7e provided at bobbin 7.

Figure 3A:
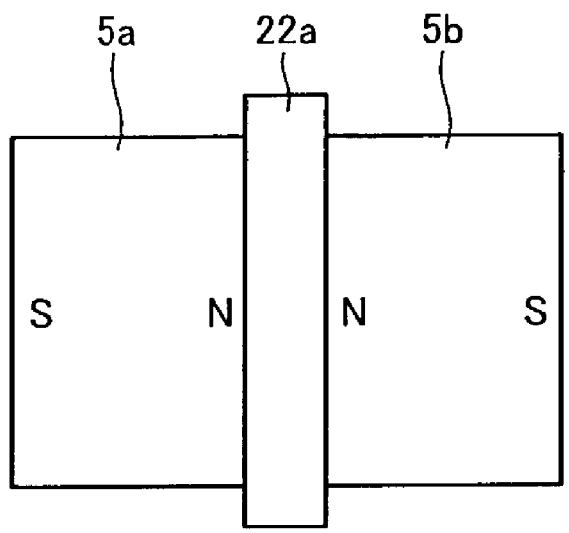
FIGS. 3A and 3B illustrate arrangement of permanent magnets and a yoke in the relevant flow control valve.
Figure 3B:
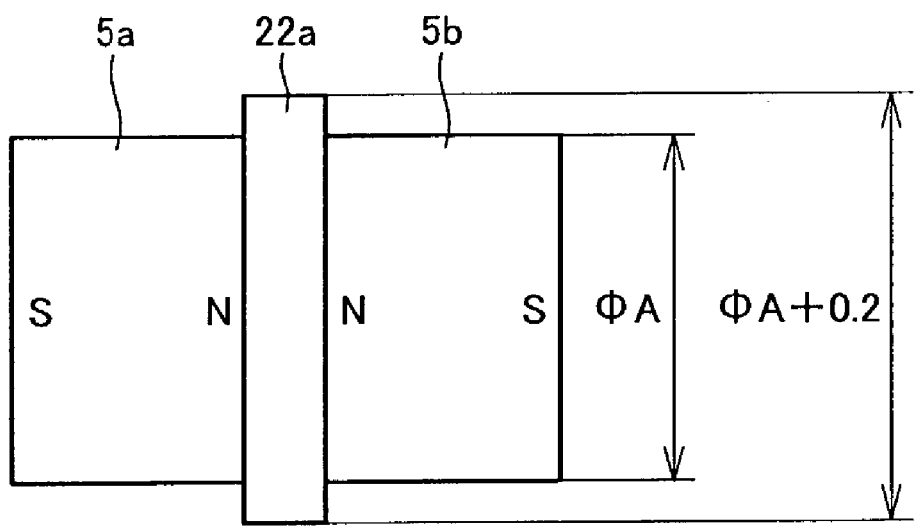

Permanent magnets 5a, 5b are arranged next to each other with a yoke 22a sandwiched therebetween such that the same poles (here, N poles) confront each other, as shown in FIGS. 3A, 3B. More specifically, here, permanent magnet 5a has the S pole on the left side and the N pole on the right side of FIG. 1A, and permanent magnet 5b has the N pole on the left side and the S pole on the right side. Yoke 22a located between permanent magnets 5a, 5b is excited by the N poles of respective permanent magnets 5a, 5b. In this case, the both end surfaces of yoke 22a protrude outward from the opposing surfaces (N pole surfaces) of permanent magnets 5a, 5b. In other words, yoke 22a, here of a circular plate shape, has an outer diameter that is set greater than the outer diameters of permanent magnets 5a, 5b, here of cylindrical shapes, such that the peripheral portion of yoke 22a protrudes from permanent magnets 5a, 5b. This further facilitates the placement of permanent magnets 5a, 5b with the same poles facing each other, compared to the case where the permanent magnets and the yoke have the same diameters.

The outer diameters of yoke 22a and permanent magnets 5a, 5b are set such that the outer diameter of the yoke becomes $\phi A+0.2$ mm when the outer diameter of each permanent magnet is $\phi A$. Specifically, when the outer diameter $\phi A$ of each permanent magnet is 7.8 mm or 8.8 mm, the outer diameter of the yoke is 8.0 mm or 9.0 mm, respectively. When a difference between their outer diameters is not less than +0.2 mm, adhesion of the permanent magnets to the yoke becomes unnecessary, so that the ease of assembly increases.

Figure 4A:
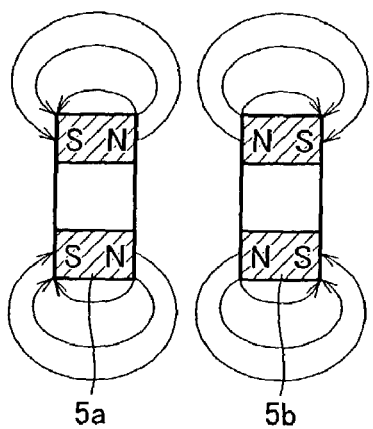
FIG. 4A shows distribution of magnetic flux when two permanent magnets are arranged with the same poles confronting each other.
Figure 4B:
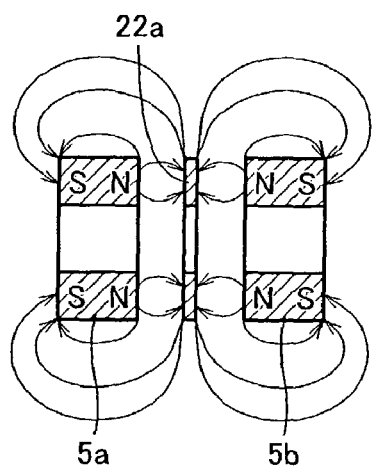
FIG. 4B shows distribution of magnetic flux when a yoke is arranged between the permanent magnets.
Figure 4C:
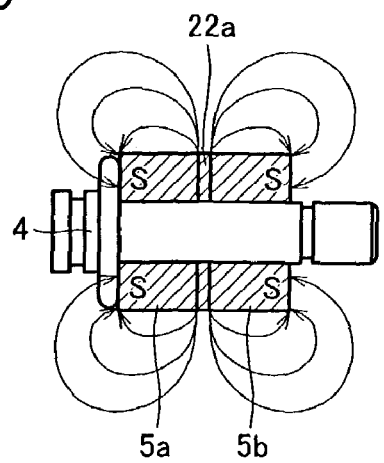
FIG. 4C shows distribution of magnetic flux when the permanent magnets support the yoke by sandwiching it therebetween.

In addition, by arranging permanent magnets 5a, 5b next to each other with yoke 22a directly sandwiched therebetween (FIG. 4C), the magnetic forces of permanent magnets 5a, 5b can be utilized most effectively compared to the case where permanent magnets 5a, 5b are arranged simply opposite to each other (FIG. 4A) and further to the case where yoke 22a is arranged between permanent magnets 5a, 5b with spaces provided therebetween (FIG. 4B).

An elastic body 21a arranged opposite to the end surface of permanent magnet 5a is herein supported by actuating shaft 4 and permanent magnet 5a as it is sandwiched therebetween. An elastic body 21b arranged opposite to the end surface of permanent magnet 5b is sandwiched between and hence supported by retaining ring 24 and permanent magnet 5b.

Bobbin 7 is arranged around permanent magnets 5a, 5b, and is provided with three magnet coils 6a, 6b, 6c. Here, magnet coil 6b is set slightly longer than the others. The winding direction of each magnet coil 6a, 6b, 6c is set such that actuating shaft 4 receives a combined force of the electromagnetic forces generated by respective magnet coils 6a, 6b, 6c and respective permanent magnets 5a, 5b in the direction along which the shaft moves. Specifically, the magnet coils are provided to bobbin 7 with their winding directions alternately opposite to each other. Here, the winding direction of magnet coil 6b located at the center is clockwise, while the winding direction of magnet coils 6a, 6c at respective ends is anti-clockwise. As such, current flows through magnet coil 6b in a direction opposite to the direction in which current flows through its neighboring magnet coils 6a, 6c. Magnet coils 6a, 6b, 6c are connected to an external terminal 11.

Permanent magnets 5a, 5b are arranged approximately in symmetry with respect to a central portion 40 of magnet coil 6b in the middle. A yoke 23 is provided around three magnet coils 6a, 6b, 6c so that magnet coils 6a, 6b, 6c, permanent magnets 5a, 5b, actuating shaft 4 and fixed shaft 12 are located inside the cylindrical yoke 23. Further, actuating shaft 4 is connected to frame case 2 via a damper 9. The spring action of damper 9 urges the actuating shaft to the right in FIG. 1A.

Figure 5A:
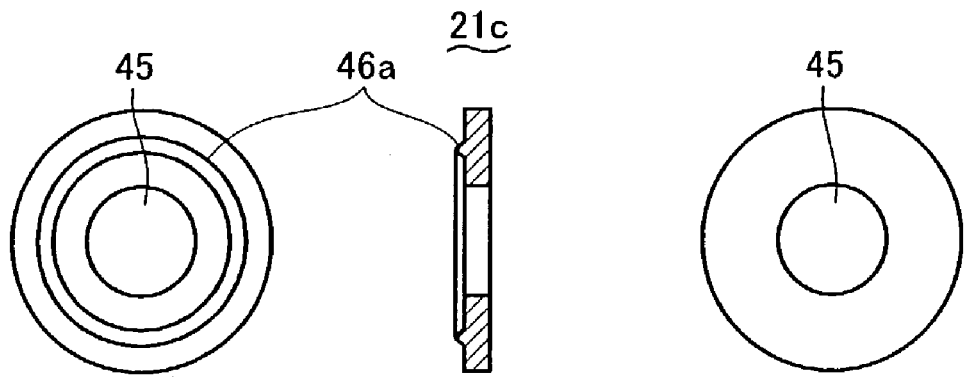
FIGS. 5A, 5B and 5C show various forms of elastic bodies in the relevant flow control valve.
Figure 5B:
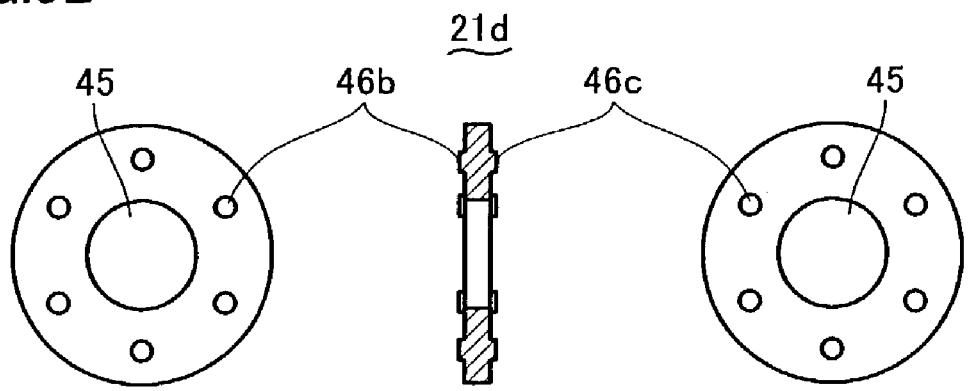
Figure 5C:
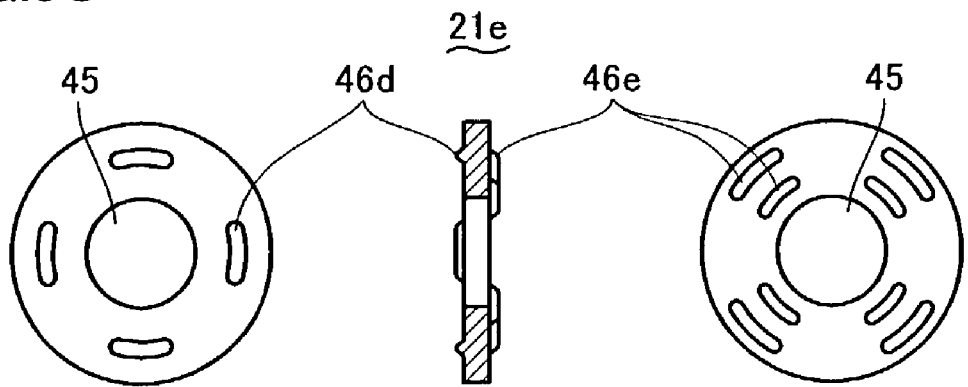

Although elastic bodies 21a, 21b arranged in contact with the respective end surfaces of permanent magnets 5a, 5b may have flat end surfaces, it is more preferable to provide readily deformable projection(s) on one or both end surfaces thereof, as shown in FIGS. 5A, 5B. The elastic body 21c shown in FIG. 5A has one ring-shaped projection 46a on one end surface. The elastic body 21d shown in FIG. 5B has six projections 46b, 46c on each end surface. The elastic body 21e shown in FIG. 5C has four longish projections 46d on one end surface, and four longer and four shorter projections 46e on the other end surface. A hole 45 is formed at the center of each elastic body 21c–21e through which actuating shaft 4 is to be passed.

By provision of such elastic bodies 21a–21e, the impact experienced when actuating shaft 4 moves to the left in FIG. 1A and orifice packing 3 abuts inflow port 1a, the impact when actuating shaft 4 abuts stopper 7e of bobbin 7, and the shock when the flow control valve is dropped are absorbed by elastic bodies 21a–21e, so that chipping, breakage or other damages of permanent magnets 5a, 5b can be avoided.

In particular, with elastic bodies 21c–21e having readily deformable projections 46a–46e, the projections 46a–46e deform and essentially fill the gaps due to the dimensional variation of the elastic bodies themselves and of permanent magnets 5a, 5b and yoke 22a placed between the elastic bodies, thereby preventing the parts from jouncing.

With the flow control valve as configured above, fixed shaft 12 of a rod shape, actuating shaft 4 of a cylindrical shape, and permanent magnets 5a, 5b, yoke 22a, elastic bodies 21a, 21b and magnet coils 6a, 6b, 6c each of a ring shape are positioned concentrically. This facilitates the assembly, and also enables more efficient utilization of the electromagnetic forces by permanent magnets 5a, 5b and magnet coils 6a, 6b, 6c, so that the thrust of actuating shaft 4 can be derived to the fullest extent. Of course, fixed shaft 12 of a non-magnetic body does not affect the electromagnetic forces.

An operation of the flow control valve as configured above is now described with reference to FIGS. 6A–6C and FIGS. 7A, 7B. Firstly, external terminal 11 causes a current of a predetermined level to flow through magnet coils 6a, 6b, 6c, so that electromagnetic forces are generated by respective magnet coils 6a, 6b, 6c and respective permanent magnets 5a, 5b, and thrusts 30a–30d act on permanent magnets 5a, 5b in the directions shown by corresponding arrows.

Figure 6A:
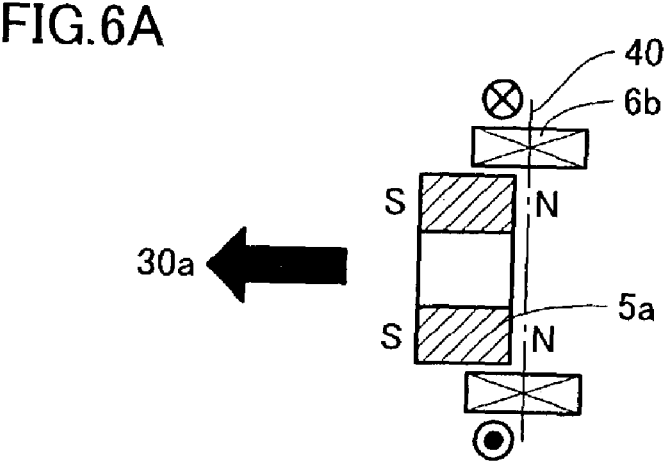
FIG. 6A shows a thrust by an electromagnetic force acting on the permanent magnet on the left-hand side and the magnet coil in the middle.
Figure 6B:
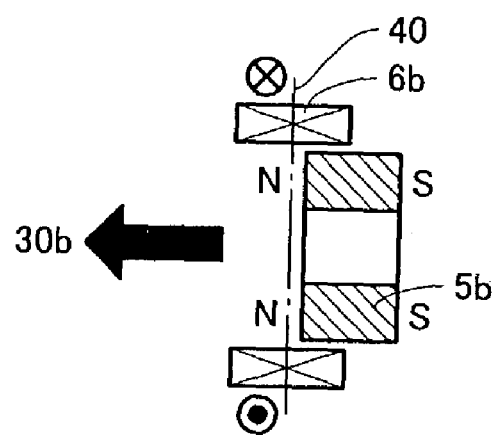
FIG. 6B shows a thrust by the electromagnetic force acting on the right-hand permanent magnet and the middle magnet coil.
Figure 6C:
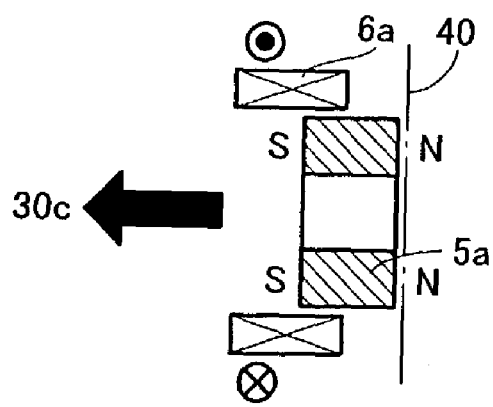
FIG. 6C shows a thrust by the electromagnetic force acting on the left-hand permanent magnet and the left-hand magnet coil in the relevant flow control valve.
Figure 7A:
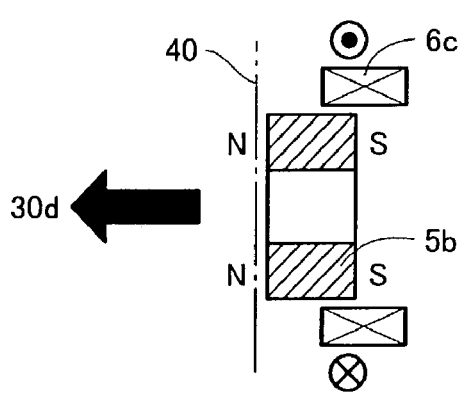
FIG. 7A shows a thrust by the electromagnetic force acting on the right-hand permanent magnet and the right-hand magnet coil.
Figure 7B:
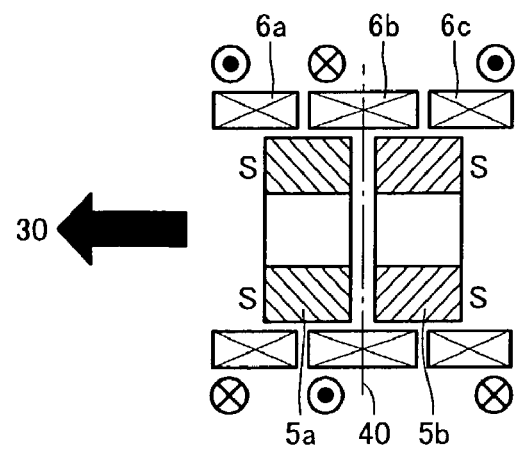
FIG. 7B shows a combined thrust by the electromagnetic forces acting on the two permanent magnets and three magnet coils as a whole in the relevant flow control valve.

FIG. 6A shows thrust 30a that is generated with the electromagnetic force by permanent magnet 5a and magnet coil 6b. FIG. 6B shows thrust 30b generated with the electromagnetic force by permanent magnet 5b and magnet coil 6b. FIG. 6C shows thrust 30c generated with the electromagnetic force by permanent magnet 5a and magnet coil 6a. FIG. 7A shows thrust 30d generated with the electromagnetic force by permanent magnet 5b and magnet coil 6c. That is, permanent magnet 5a receives thrusts 30a, 30c by the electromagnetic forces acting by magnetic coils 6a, 6b, and permanent magnet 5b receives thrusts 30b, 30d by the electromagnetic forces acting by magnet coils 6b, 6c.

As shown in the respective figures, the repelling and attracting actions of the poles between permanent magnets 5a, 5b and magnet coils 6a, 6b, 6c are utilized to cause the thrusts to act on permanent magnets 5a, 5b both in the left direction. The respective thrusts 30a–30d are combined to form one large thrust 30 (FIG. 7B), so that actuating shaft 4 to which permanent magnets 5a, 5b are attached overcomes the repulsive force of damper 9, and aggressively moves to the left. This causes orifice packing 3 to abut gas inflow port 1a (see FIG. 8B), so that inner tube 1 attains a completely blocked state.

As such, thrust 30 acting on actuating shaft 4 is the combined force of the thrusts acting on respective permanent magnets 5a, 5b. Thus, a strong thrust can be obtained by the electromagnetic forces even with small permanent magnets.

After inner tube 1 has attained the blocked state, the supply current to magnet coils 6a, 6b, 6c is gradually decreased. In response, the electromagnetic force is progressively reduced, and the thrusts applied to permanent magnets 5a, 5b decrease correspondingly. Actuating shaft 4 gradually moves to the right due to the elasticity of damper 9 and the slant repulsive action of orifice packing 3, so that orifice packing 3 slowly moves away from inflow port 1a. As a result, inflow port 1a is opened in a minute and continuous manner, and finally attains a completely open state (see FIG. 8A).

Further, actuating shaft 4 linearly moves with respect to inflow port 1a while being guided along fixed shaft 12. This eliminates wasteful movement or jouncing of actuating shaft 4 to which permanent magnets 5a, 5b, yoke 22a and others are attached. When applied to a blood pressure gauge as will be described later, it enables minute and continuous control of exhaust flow rate, with excellent operative reproducibility.

In addition, since actuating shaft 4 has air vent 4b communicating with hollow portion 4d, the air flows into hollow portion 4d through air vent 4b as actuating shaft 4 moves leftward, so that negative pressure does not build up in hollow portion 4d. This prevents application of counterforce to actuating shaft 4. On the other hand, when actuating shaft 4 moves rightward, the air escapes from hollow portion 4d via air vent 4b, again preventing application of counterforce to actuating shaft 4. Since the air in hollow portion 4d does not suffer expansion, compression or other phenomena, actuating shaft 4 can move smoothly in the absence of air resistance.

Figure 9A:
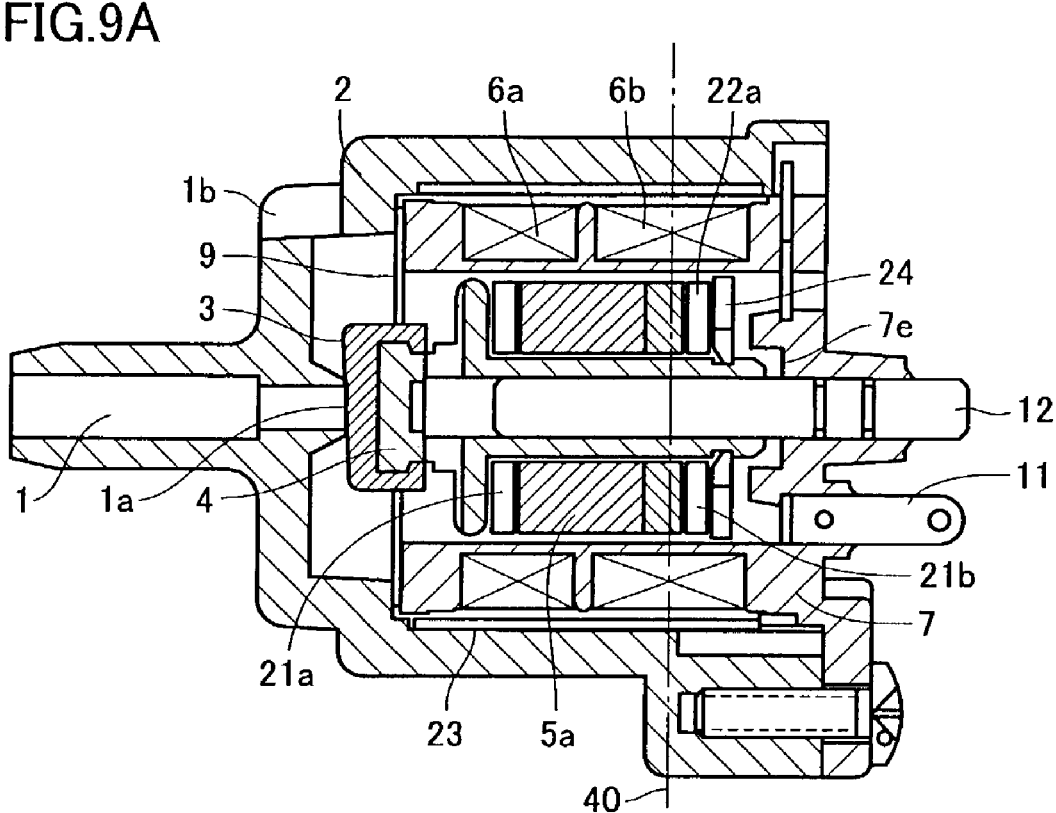
FIG. 9A is a schematic cross sectional view of the flow control valve according to another embodiment of the present invention.
Figure 9B:
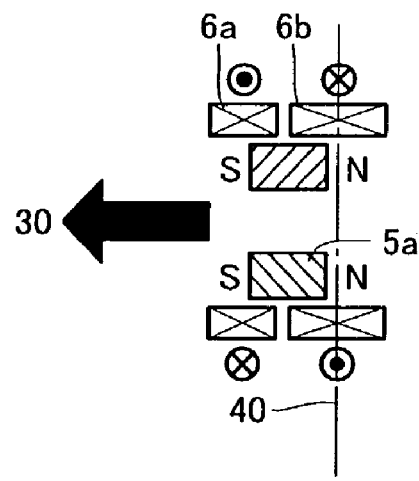
FIG. 9B shows a combined thrust by the electromagnetic forces acting on one permanent magnet and two magnet coils as a whole.

The flow control valve according to another embodiment of the present invention is shown in FIG. 9A (schematic cross sectional view) and FIG. 9B (showing interaction of a permanent magnet and magnet coils). The same elements as in the above-described embodiment are denoted by the same reference characters, and description thereof is not repeated. This flow control valve uses one permanent magnet 5a and two magnet coils 6a, 6b. Here, although only one permanent magnet 5a is employed, a yoke 22a is arranged on the rear end surface (N pole side) of permanent magnet 5a. Magnet coil 6b is longer than magnet coil 6a, and permanent magnet 5a is located on the left side with respect to the central portion 40 of magnet coil 6b.

This flow control valve enjoys the same functions and effects as described above. That is, when a current is passed through magnet coils 6a, 6b, permanent magnet 5a receives a thrust 30 by the electromagnetic forces acting on magnet coils 6a, 6b. Actuating shaft 4 moves to the left, so that inflow port 1a is closed by orifice packing 3.

Figure 10A:
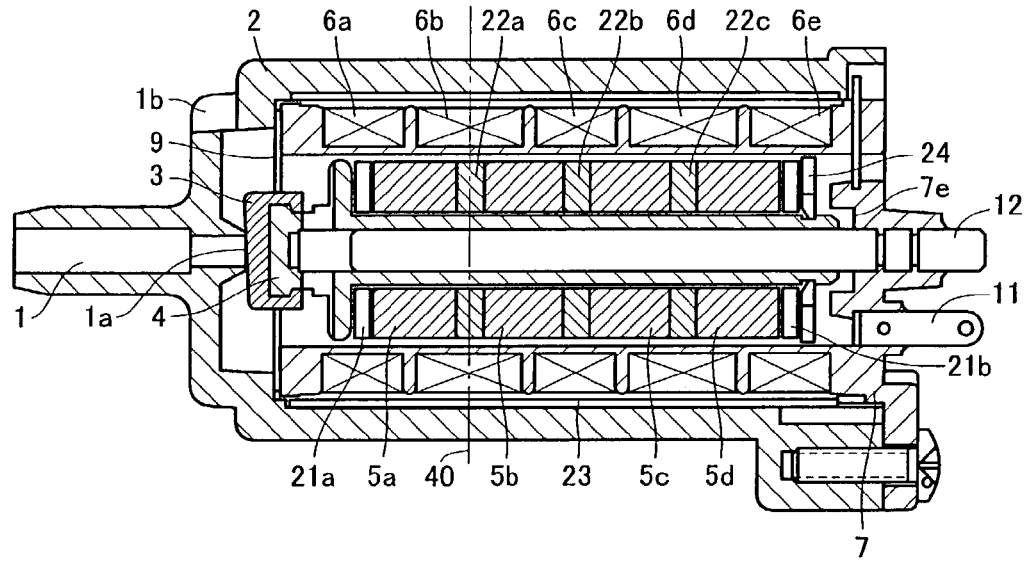
FIG. 10A is a schematic cross sectional view of the flow control valve according to still another embodiment of the present invention.
Figure 10B:
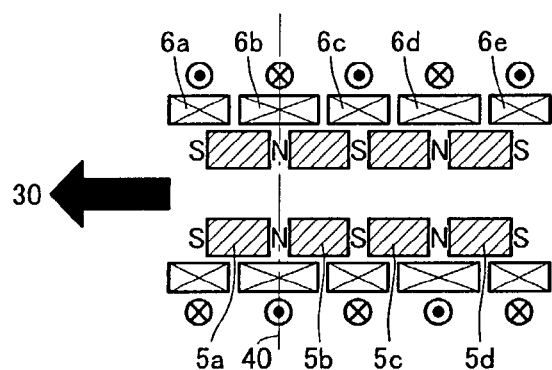
FIG. 10B shows a combined thrust by the electromagnetic forces acting on four permanent magnets and five magnet coils as a whole.

The flow control valve according to still another embodiment of the present invention is shown in FIG. 10A (schematic cross sectional view) and FIG. 10B (showing interaction of permanent magnets and magnet coils). This flow control valve uses four permanent magnets 5a, 5b, 5c, 5d and five magnet coils 6a, 6b, 6c, 6d, 6e, and yokes 22a, 22b, 22c are arranged between respective permanent magnets 5a, 5b, 5c, 5d. Magnet coils 6b, 6d are longer than the other coils. Permanent magnet 5a is located on the left side with respect to the central portion 40 of magnet coil 6b, while the remaining permanent magnets 5b, 5c, 5d are located on the right side.

With this flow control valve, again, when a current is passed through magnet coils 6a, 6b, 6c, 6d, 6e, actuating shaft 4 moves as it receives the thrust 30 to the left direction caused by the electromagnetic force.

Figure 11A:
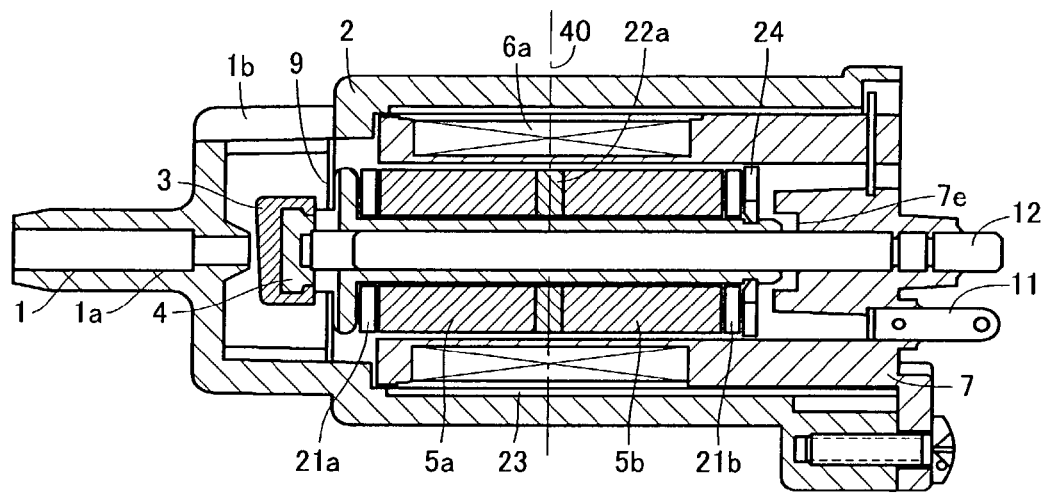
FIG. 11A is a schematic cross sectional view of the flow control valve according to yet another embodiment of the present invention.
Figure 11B:
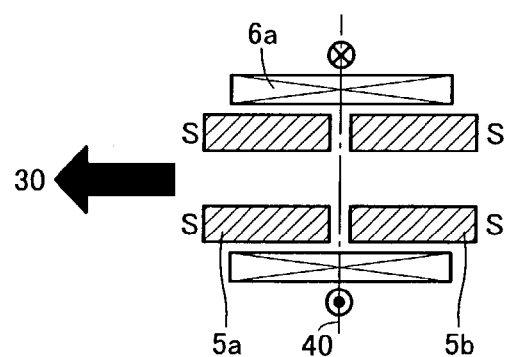
FIG. 11B shows a combined thrust by the electromagnetic forces acting on two permanent magnets and one magnet coil as a whole.

The flow control valve according to yet another embodiment of the present invention is shown in FIG. 11A (schematic cross sectional view) and FIG. 11B (showing interaction of permanent magnets and a magnet coil). This flow control valve uses two permanent magnets 5a, 5b and one magnet coil 6a. Here, both permanent magnets 5a, 5b are relatively long, and correspondingly, magnet coil 6a is elongated. Yoke 22a is located exactly at the central portion 40 of magnet coil 6a, and permanent magnets 5a, 5b are arranged symmetrically on respective sides of central portion 40.

With this flow control valve, again, when a current is passed through magnet coil 6a, actuating shaft 4 moves as it receives the leftward thrust 30 by the electromagnetic force.

Figure 12:
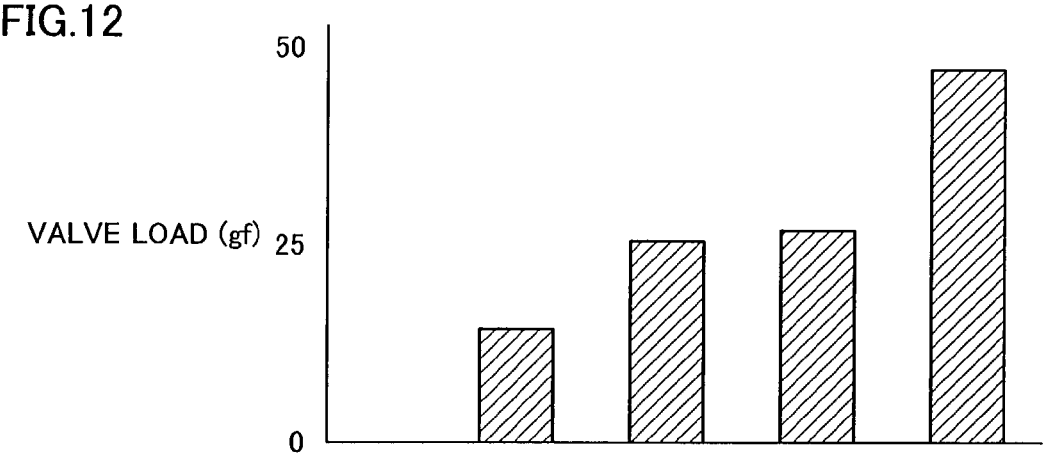
FIG. 12 shows by means of graphs valve loads obtained by the respective flow control valves shown in FIGS. 1A and 1B, FIGS. 9A and 9B and FIGS. 11A and 11B, and a conventional flow control valve.

The flow control valves of the above embodiments each exert a pressing force on gas inflow port 1a that is stronger than in the case of a conventional valve using one permanent magnet and one magnet coil, as shown in FIG. 12. FIG. 12 shows, by graphs, valve loads (gf) obtained by the conventional valve having one magnetic coil and one permanent magnet, obtained by the embodiment shown in FIGS. 11A, 11B having one magnet coil and two permanent magnets, obtained by the embodiment shown in FIGS. 9A, 9B having two magnet coils and one permanent magnet, and obtained by the embodiment shown in FIGS. 1A, 1B having three magnet coils and two permanent magnets. The valve load represents the force with which the central portion of orifice packing 3 presses gas inflow port 1a, which was measured under the same current and the same duty ratio. It is apparent from the graphs that the valve loads of the embodiments of the present invention are greater than that of the conventional case, and that the valve load increases as the numbers of magnet coils and permanent magnets increase.

Figure 13:
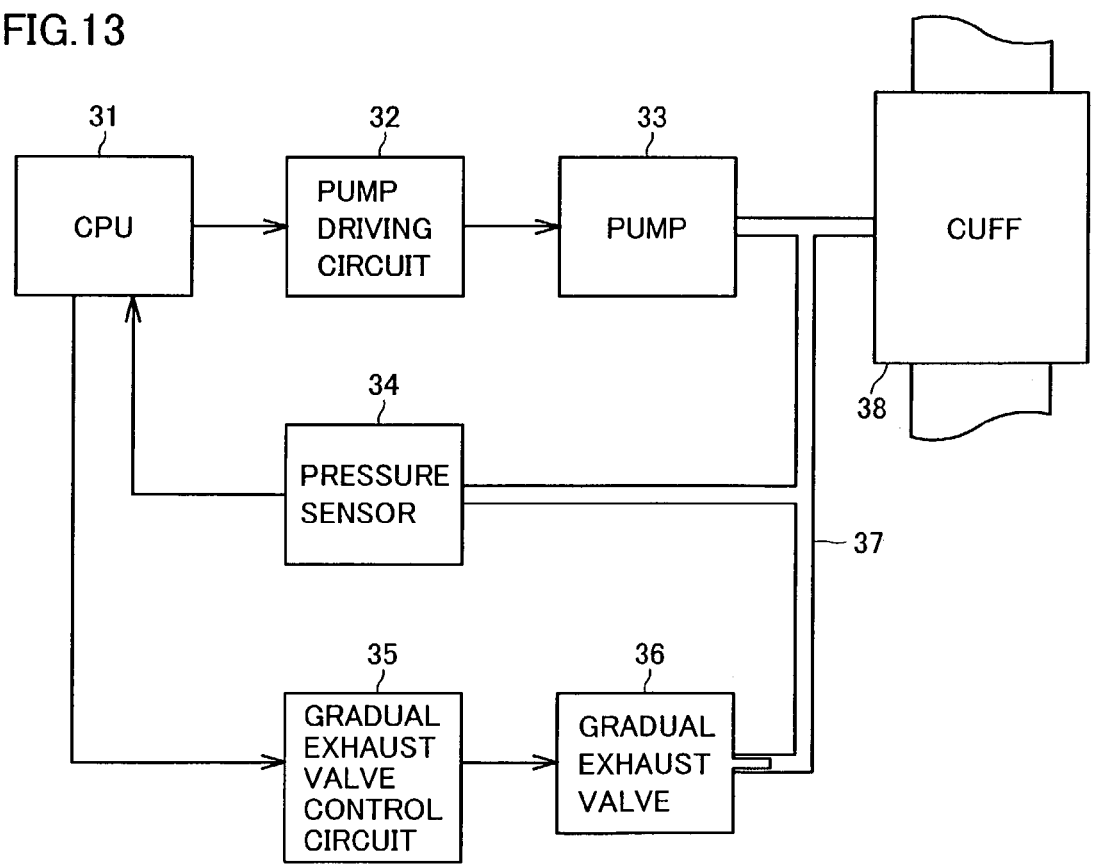
FIG. 13 is a block diagram showing a schematic configuration of a blood pressure gauge provided with the flow control valve according to an embodiment of the present invention.

Now, a case where the flow control valve as in the above-described embodiments is adapted to a blood pressure gauge is explained by way of example. FIG. 13 is a block diagram showing a schematic configuration of the blood pressure gauge. The flow control valve is used as a gradual exhaust valve 36 in this block diagram. A CPU 31 carries out control of the entire blood pressure gauge and others. A pump driving circuit 32 drives a pump 33 in accordance with a command of CPU 31. Pump 33 is driven by pump driving circuit 32 and supplies air to a cuff 38 via a tube 37. A pressure sensor 34 detects the pressure of the air supplied to cuff 38. A gradual exhaust valve control circuit 35 controls gradual exhaust valve 36 in accordance with a command of CPU 31. Opening/closing of gradual exhaust valve 36 is controlled by gradual exhaust valve control circuit 35 to adjust the air pressure within tube 37. Cuff 38 is provided with the air from pump 33 via tube 37. The above-described flow control valve as the gradual exhaust valve 36 is connected to the airflow path system as the tube 37 is fitted to the outside of inner tube 1.

Figure 14:
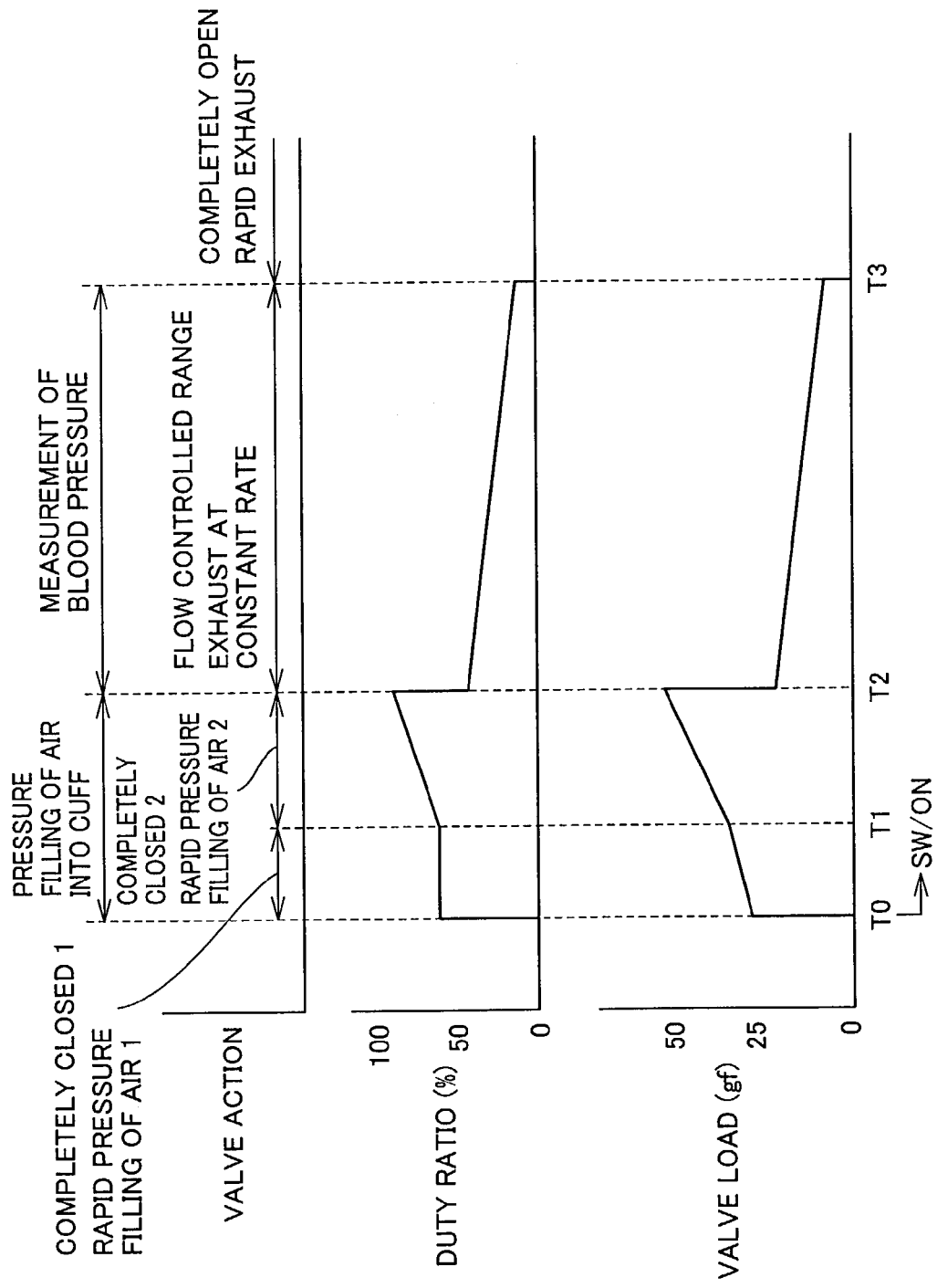
FIG. 14 is a timing chart illustrating an operation of the blood pressure gauge having the configuration shown in FIG. 13.

The operation of the blood pressure gauge as configured above is now explained with reference to the timing chart shown in FIG. 14. In FIG. 14, the valve load shown at the bottom indicates the force with which the central portion of orifice packing 3 presses gas inflow port 1a. The duty ratio shown in the middle is that of the pulse voltage applied to magnet coils 6a, 6b, 6c (see FIG. 1A) via external terminal 11. The valve action at the top represents the action of gradual exhaust valve 36. These three properties share the common horizontal axis (time axis).

Firstly, at time T0, a power switch (S/W), not shown, is turned ON. Pump driving circuit 32 drives pump 33 in accordance with a command of CPU 31, and starts air supply to cuff 38. At the same time gradual exhaust valve control circuit 35 controls gradual exhaust valve 36 in accordance with a command of CPU 31, and applies a pulse voltage with a frequency of 31.25 kHz and a duty ratio of 60%, for example. Application of the pulse voltage with the relevant frequency and duty ratio is continued till time T1. Thus, orifice packing 3 in FIG. 1 continuously blocks gas inflow port 1a with a pressing force in proportion to an average level of the pulse voltage, and the valve load increases, e.g., from about 25 gf to about 30 gf over time from T0 to T1. During this time period, gradual exhaust valve 36 is in a completely closed state ("completely closed 1" at the top of FIG. 14) and the air is rapidly pressure filled into cuff 38 ("rapid pressure filling of air 1" at the top of FIG. 14). Pump 33 is continuously driven till time T2.

From time T1, the duty ratio of the pulse voltage is gradually increased such that the duty ratio becomes about 90% at time T2. In response, the valve load gradually increases, e.g., from about 30 gf to about 45 gf. During this time period, gradual exhaust valve 36 keeps the completely closed state ("completely closed 2" at the top of FIG. 14), and the air is rapidly pressure filled in cuff 38 ("rapid pressure filling of air 2" at the top of FIG. 14). As such, the air is pressure filled into cuff 38 during the time period from T0 to T2 ("pressure filling of air into cuff" at the top of FIG. 14).

At time T2, pump 33 is stopped according to a command of CPU 31. At the same time, the duty ratio of the pulse voltage is reduced to about 40% in a stroke, and thereafter, it is gradually decreased so that it becomes about 10% at time T3. The valve load is also decreased at time T2 in one stroke from about 45 gf to about 20 gf, for example, and it is then gradually decreased from about 20 gf to about 5 gf over time from T2 to T3. During this time period, gradual exhaust valve 36 is in a flow controlled state ("flow controlled range" at the top of FIG. 14), and the air is exhausted from cuff 38 at a constant rate ("exhaust at constant rate" at the top of FIG. 14). The blood pressure is measured in this process ("measurement of blood pressure" at the top of FIG. 14).

At time T3, the duty ratio of the pulse voltage is decreased to 0% in a stroke according to a command of CPU 31. At this time, orifice packing 3 is completely disengaged from gas inflow port 1*a*, so that gradual exhaust valve 36 attains a completely open state, and the air is rapidly exhausted from cuff 38 ("completely open, rapid exhaust" at the top of FIG. 14).

It is needless to say that the flow control valves shown in the respective embodiments are only by way of example, and the present invention is not limited thereto. For example, in the flow control valves shown in FIGS. 1A, 1B, FIGS. 9A, 9B, FIGS. 10A, 10B and FIGS. 11A, 11B, the permanent magnet(s) may be arranged oppositely in polarity and the current may be passed through the magnet coil(s) in the opposite directions, in which case exactly the same functions and effects are obtained. Further, although the gas inflow port 1*a* has been configured to open/close by means of orifice packing 3, a tapered packing may be inserted into gas inflow port 1*a* instead.

As explained above, according to the flow control valve of the present invention, it is possible to cause a combination of the electromagnetic forces generated by respective magnet coils and respective permanent magnets to act on a moving member. Thus, compared to the conventional case using one permanent magnet and one magnet coil, the thrust to move the moving member is considerably increased, and the force with which an open/close member attached to the moving member presses the gas inflow port is increased remarkably. As a result, the thrust of the moving member can be increased with the valve of the conventional size, or, if the thrust of the conventional level will suffice, the valve can be downsized. Accordingly, a compact flow control valve with a simple structure, consuming less power and suffering less malfunction, and yet fully deriving and effectively utilizing the thrust by the electromagnetic force, is provided.

Further, a blood pressure gauge provided with such a flow control valve as air exhaust means is improved in exhaust performance, becomes compact and consumes less power.

By provision of the fixed shaft guiding the moving member only in directions opening/closing the gas inflow port, the moving member linearly moves toward and away from the gas inflow port along the fixed shaft, with wasteful movement and jouncing being eliminated. When applied to a blood pressure gauge, minute and continuous control of exhaust flow rate is enabled, with excellent operative reproducibility.

Although the present invention has been described with reference to various embodiments, it should be understood that the embodiments disclosed herein are illustrative and non-restrictive in every respect. The scope of the present invention is defined by the terms of the appended claims, and is intended to include any modifications within the scope and meaning equivalent thereto.

What is claimed is:

1. A flow control valve, comprising:

a housing having a gas inflow port and a gas outflow port which communicates with the gas inflow port through an internal space;

a moving member which is arranged inside the housing and is movable toward and away from said gas inflow port;

an open/close member arranged on a portion of the moving member opposite to the gas inflow port such that the movement of the moving member opens/closes said gas inflow port; and at least one magnetic coil and a plurality of permanent magnets arranged within the housing to move the moving member, the moving member being made to move with an electromagnetic force generated by said at least one magnet coil and said permanent magnets such that the gas inflow port is opened/closed by the open close member to control an air flow rate;

wherein a yoke made of a magnetic substance is placed between at least one pair of the permanent magnets; and said yoke has end surfaces protruding outward from opposing surfaces of said permanent magnets.

2. A flow control valve comprising:

a housing having a gas inflow port and a gas outflow port which communicates with the gas inflow port through an internal space;

a moving member which is arranged inside the housing and is movable toward and away from said gas inflow port;

an open/close member arranged on a portion of the moving member opposite to the gas inflow port such that the movement of the moving member opens/closes said gas inflow port; and at least one magnetic coil and a plurality of permanent magnets arranged within the housing to move the moving member the moving member being made to move with an electromagnetic force generated by said at least one magnet coil and said permanent magnets such that the gas inflow port is opened/closed by the open close member to control an air flow rate;

wherein a yoke made of a magnetic substance is placed between at least one pair of the permanent magnets;

said permanent magnets and said yoke are arranged and attached in series to the moving member, and move together with the moving member; and elastic bodies are arranged opposite to outer end surfaces of the permanent magnets located at both outer ends of said permanent magnets arranged and attached in series.

3. The flow control valve according to claim 2, wherein said elastic bodies have a readily deformable projection on an end surface thereof.

* * * * *